(12) United States Patent
Wang et al.

(10) Patent No.: US 11,985,929 B2
(45) Date of Patent: May 21, 2024

(54) HAND-HELD PNEUMATIC POLLINATOR FOR HYBRID RICE SEED PRODUCTION AND METHOD THEREOF

(71) Applicant: ZHEJIANG UNIVERSITY, Zhejiang (CN)

(72) Inventors: Yongwei Wang, Hangzhou (CN); Fuqiang Yao, Hangzhou (CN); Yifeng Hao, Hangzhou (CN); Jun Wang, Hangzhou (CN); Zhenbo Wei, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 342 days.

(21) Appl. No.: 17/340,105

(22) Filed: Jun. 7, 2021

(65) Prior Publication Data
US 2021/0289729 A1 Sep. 23, 2021

Related U.S. Application Data

(63) Continuation of application No. PCT/CN2020/122127, filed on Oct. 20, 2020.

(51) Int. Cl.
*A01H 1/02* (2006.01)
(52) U.S. Cl.
CPC .................................. *A01H 1/027* (2021.01)
(58) Field of Classification Search
CPC . A01H 1/02; A01H 1/027; A01H 1/04; A01H 1/00; A01H 6/54; A01G 7/06;
(Continued)

(56) References Cited

U.S. PATENT DOCUMENTS

| 4,383,389 A | 5/1983 | Vradenburg |
| 8,375,690 B2 * | 2/2013 | LaFargue ............... A01D 45/00 56/13.1 |

(Continued)

FOREIGN PATENT DOCUMENTS

| CN | 102812900 A | 12/2012 |
| CN | 202958391 U | 6/2013 |

(Continued)

OTHER PUBLICATIONS

International Search Report (PCT/CN2020/122127); dated Jan. 25, 2021.

(Continued)

*Primary Examiner* — Ebony E Evans
(74) *Attorney, Agent, or Firm* — W&G Law Group

(57) ABSTRACT

A hand-held pneumatic pollinator for hybrid rice seed production and a method thereof are provided. The pollinator includes a hand-held power chassis, a lifting assembly, a pneumatic pollination assembly, and a control assembly. A position of each of air blowing pipes relative to an ear of the male parent is adjusted by the control assembly and the lifting assembly. The pneumatic pollination assembly is provided with a plurality of air blowing pipes, of which the number is less than rows of the male parent of a hybrid rice seed production with a relatively large row ratio. Each air blowing pipe is located between corresponding two rows of the male parent during pollination. The directional, uniform and constant airflow at an air blowing port blows a pollen off a stamen to transport the pollen to the female parent compartment.

7 Claims, 4 Drawing Sheets

(58) Field of Classification Search
CPC ........ A01G 17/00; A01G 22/40; A01G 13/06; A01B 76/00
See application file for complete search history.

(56) References Cited

U.S. PATENT DOCUMENTS

| | | | | |
|---|---|---|---|---|
| 9,943,049 | B2* | 4/2018 | Safreno | ......... A01H 1/027 |
| 2006/0053686 | A1* | 3/2006 | Halwas | ......... A01H 1/027 |
| | | | | 47/1.41 |

FOREIGN PATENT DOCUMENTS

| CN | 103250629 A | 8/2013 |
|---|---|---|
| CN | 103250630 A | 8/2013 |
| CN | 103250631 A | 8/2013 |
| CN | 103262786 A | 8/2013 |
| CN | 106258943 A | 1/2017 |
| CN | 110214690 A | 9/2019 |
| CN | 111202001 A | 5/2020 |
| FR | 2979798 B1 | 4/2014 |
| SU | 1429997 A1 | 10/1988 |
| WO | 2018129302 A1 | 7/2018 |
| WO | 2019241419 A1 | 12/2019 |

OTHER PUBLICATIONS

Notice of Allowance(CN202010121683.1); dated Apr. 22, 2021. Optimization-on-structure-and-parameters-of-a-collision-pneumatic-hybrid-rice-pollination-machine.

* cited by examiner

HAND-HELD PNEUMATIC POLLINATOR FOR HYBRID RICE SEED PRODUCTION AND METHOD THEREOF

CROSS-REFERENCE TO RELATED APPLICATIONS

The present application is a continuation of International Application No. PCT/CN2020/122127, which claims priority to Chinese Patent Application No. 202010121683.1, each of which is incorporated by reference in its entirety.

TECHNICAL FIELD

The present disclosure relates to a hand-held pneumatic pollinator for hybrid rice seed production, in particular, to a pneumatic pollination device with a large row ratio of male and female parents and a method thereof, which are suitable for large-scale seed production.

BACKGROUND

China is the birthplace of hybrid rice and the main producing area of hybrid rice seeds. In 2017, China has hybrid rice seed production area of about 160,000 hectares with an annual output of more than 280 million kilograms of seeds, and the seeds have achieved large-scale production. However, pollination is an operation with high technical and precision requirements as well as urgent time requirements. The rice has a relatively short pollen florescence with a full florescence of only 7 to 10 days, and generally only 1.5 to 2 hours of florescence in one day. Thus, it is necessary to complete the pollination operation within a limited time. Artificial assisted pollination includes manual pollination and mechanical pollination. So far, the mechanical pollinator is not popularized and applied, and the manual pollination is still the main pollination method. The manual pollination mainly includes a single-long-rod pollen pushing, a double-short-rod pollen pushing and a rope pollen pulling. The single-long-rod pollen pushing and the double-short-rod pollen pushing are pollination methods for pushing male parents to female parents so that the pollen sheds and scatters to the stigmas of the female parents, and are suitable for the pollination of the plant with plant row ratios, such as, 1:3, 1:4, 2:6 and 2:8, for male and female parents and the like. In these pollination methods, the harvested seeds are of higher quality and higher yield. However, the labor intensity is high and the productivity is low, which is not compatible with the requirements of modern large-scale seed production. The rope pollen pulling is a pollination method in which two people pull the ends of a rope and run on both sides of the farm to push the male parents to the female parents by the rope, such that the pollen will float to the stigmas of the female parents. Since there is no suitable pollination device, this pollination method is an obligatory choice for improving productivity. However, this pollination method has high labor intensity, low pollen utilization rate and large yield loss. Although the traditional manual pollination method is simple and easy to implement, it has problems such as high labor intensity, low efficiency, damage to the plants, obvious uneven pollination, and reduced seed production, which no longer meets the requirements of modern seed production. The mechanical pollination includes a collision pollination and a pneumatic pollination. The collision pollination mainly simulates the manual rod "pollen pushing" to shake off the pollen and spread it to the female parents so as to achieve the pollination. However, in this pollination method, the pollen is substantially scattered at the plants near the male parents. Further, this pollination method has short spreading distance and uneven distribution, and the plants are easily damaged during the collision, which does not meets the requirements of modern seed industry for efficient pollination. The pneumatic pollination can generate a continuous and stable airflow by a fan to blow the pollen away from the stamens and fall on the stigmas of the pistils, thereby completing the pollination. However, there is no corresponding device at present. Therefore, a mechanized pollination device for hybrid rice seed production of a large row ratio is desired in the current hybrid rice seed production industry, so that the productivity of pollination operations is greatly improved, and the level of hybrid rice seed production mechanization, the quality and yield of hybrid rice seed production are improved, so as to effectively solve the problem of pollen directional transportation and uniform pollination in the hybrid rice seed production of the large row ratio, thereby promoting the sustainable and healthy development of the seed industry.

SUMMARY

The present disclosure aims to solve the problem of lack of mechanized pollination equipment in hybrid rice seed production at present, to meet large-scale seed production of a large row ratio. Therefore, at least some embodiments of the present disclosure provide a hand-held pneumatic pollinator for hybrid rice seed production, which causes a pollen to shed and to be directionally conveyed by each air blowing pipe to act with corresponding female parent region, to achieve directional, uniform and efficient pollination.

According to one aspect of the present disclosure, there is provided a hand-held pneumatic pollinator for hybrid rice seed production including a hand-held power chassis, a lifting assembly, a pneumatic pollination assembly and a control assembly, wherein the lifting assembly and the control assembly are fixed at an upper portion of the hand-held power chassis, and the pneumatic pollination assembly is fixed at the front of the lifting assembly and is controlled by the lifting assembly to move upwardly and downwardly;

wherein the hand-held power chassis includes an engine, a centrifugal clutch, support wheels, driving wheels, a decelerator, a crop divider and armrests, a power output shaft of the engine is connected to a power input shaft of the decelerator by the centrifugal clutch, the driving wheels are installed on a power output shaft of the decelerator, the support wheels are fixed below the decelerator, front portions of the armrests are fixed on the decelerator, the crop divider is fixed at the front of the decelerator, and the lifting assembly is fixed on the decelerator by a bracket;

wherein the pneumatic pollination assembly includes a lifting frame, flow velocity sensors, a first right one-way air blowing pipe, a second right one-way air blowing pipe, a center two-way air blowing pipe, baffle plates, a second left one-way air blowing pipe, a first left one-way air blowing pipe, direct current fans, drive controllers, support plates, a storage battery, and right-angle sliding sleeves, wherein each of the first right one-way air blowing pipe, the second right one-way air blowing pipe, the center two-way air blowing pipe, the second left one-way blowing pipe and the first left one-way blowing pipe is L-shaped and has a vertical section with a same length, two right-angle sliding sleeves are symmetrically vertically fixed at each of the vertical sections of the first right one-way air blowing pipe, the second right one-way air blowing pipe, the center two-way air blowing pipe, the second left one-way air blowing pipe, and the first left one-way air blowing pipe at a same height, and a distance between the two right-angle sliding sleeves is same as a width of the lifting frame, and wherein the first right one-way air blowing pipe, the second right one-way air blowing pipe, the center two-way air blowing pipe, the second left one-way air blowing pipe and the first left one-way air blowing pipe are sequentially sleeved on the lifting frame through the right-angle sliding sleeves in a right to left direction and are equidistant from each other;

wherein the support plates are equidistantly fixed at an upper portion of the lifting assembly, the direct current fans are fixed at front side portions of the support plates, respectively, the drive controllers are fixed at rear side portions of the support plates, respectively, an air outlet of one of the direct current fans communicate with an upper portion of one of the first right one-way air blowing pipe, the second right one-way air blowing pipe, the center two-way air blowing pipe, the second left one-way air blowing pipe, and the first left one-way air blowing pipe through a hose;

wherein a front end of a horizontal section of each of the first right one-way air blowing pipe, the second right one-way air blowing pipe, the center two-way air blowing pipe, the second left one-way air blowing pipe, and the first left one-way air blowing pipe is provided with an air blowing port, and an lower portion of the air blowing port is provided with a baffle plate configured to form an airflow, which causes pollen of a male parent to drift to a female parent, wherein a flow velocity sensor is fixed at the vertical section of each of the first right one-way air blowing pipe, the second right one-way air blowing pipe, the center two-way air blowing pipe, the second left one-way air blowing pipe, and the first left one-way air blowing pipe at a same height, a detection end of the flow velocity sensor extends into an interior of the air blowing pipe where the flow velocity sensor is located, to measure an airflow velocity therein, and the storage battery is fixed on the bracket of the lifting assembly;

wherein the lifting assembly includes the bracket, a guide rail, a lead screw, a stepping motor, and sliders, wherein the guide rail is vertically fixed at a front upper portion of the bracket and an upper portion of the guide rail is provided with a bearing support, an upper end of the lead screw is installed on the guide rail through the bearing support located at the upper portion of the guide rail, a lower end of the lead screw is installed on a front upper portion of the bracket through the bearing support, the guide rail is parallel to a central axis of the lead screw, the stepping motor is fixed at an upper end of the guide rail, the upper end of the lead screw is coaxially fixed to and connected with an output shaft of the stepping motor, and ball nuts are sleeved on the lead screw and forms a spiral fit with the lead screw; and the guide rail is provided with the sliders, the sliders and the guide rail constitute a moving pair, front portions of the ball nuts are fixedly connected to a middle portion of the lifting frame, and rear portions of the ball nuts are fixedly connected to the sliders; and wherein the control assembly includes a controller, flow velocity sensors, drive controllers, a storage battery, a 485-conversion-TTL module, and a touch screen, wherein the storage battery is configured to supply a power to the controller and the touch screen through a voltage regulator module, the flow velocity sensors are connected to the controller through the 485-conversion-TTL module, the drive controllers are connected to the controller through control lines, the storage battery is connected to the drive controllers through cables, and one of the drive controllers are connected to one of the five direct current fans.

In some embodiments of the present disclosure, each of the first left one-way air blowing pipe and the second left one-way air blowing pipe is L-shaped, an air blowing port is provided at a side of a front portion of the horizontal section of each of the first left one-way air blowing pipe and the second left one-way air blowing pipe facing away from the center two-way air blowing pipe, and the air blowing port is a horizontally elongated slit, and the baffle plate is fixed horizontally below the air blowing port and has a triangle shape. The first right one-way air blowing pipe and the second right one-way air blowing pipe are disposed in a mirror symmetrical structure with respect to the first left one-way air blowing pipe and the second left one-way air blowing pipe, respectively.

In some embodiments of the present disclosure, the center two-way air blowing pipe is L-shaped, an air blowing port is provided at each of both sides of a front portion of the horizontal section of the center two-way air blowing pipe, and the baffle plates are horizontally fixed below the air blowing ports.

In some embodiments of the present disclosure, the first left one-way air blowing pipe, the second left one-way air blowing pipe, the center two-way air blowing pipe, the second right one-way air blowing pipe, and the first right one-way air blowing pipe are installed on the lifting frame and are located on a same plane. A line of connecting center lines of front end of the horizontal sections of the first left one-way air blowing pipe, the second left one-way air blowing pipe, the center two-way air blowing pipe, the second right one-way air blowing pipe and the first right one-way air blowing pipe is in a "V" shape protruding toward the hand-held power chassis.

In some embodiments of the present disclosure, a length difference between the horizontal sections of two adjacent ones of the first left one-way air blowing pipe, the second left one-way air blowing pipe, the center two-way air blowing pipe, the second right one-way air blowing pipe and the first right one-way air blowing pipe is 1-1.5 times of the length of the air blowing port.

According to another aspect of the present disclosure, there is provided a pollination method using the hand-held pneumatic pollinator for hybrid rice seed production according to any one of embodiments as descried above, including:

adjusting an arrangement of air blowing pipes, wherein the adjusting the arrangement of air blowing pipes includes: adjusting a lateral horizontal position of the center two-way air blowing pipe on the lifting frame in such a manner that a longitudinal center of the center two-way air blowing pipe is located on a same vertical plane as a longitudinal central plane of the hand-held pneumatic pollinator for hybrid rice seed production, the longitudinal center of the center two-way air blowing pipe is coincident with a longitudinal central plane of the driving wheels of the hand-held power chassis; adjusting each of the air blowing pipes based on a row spacing of the male parent of the hybrid rice seed production in such a manner that a spacing between center lines of adjacent horizontal sections of the first left one-way air blowing pipe, the second left one-way air blowing pipe, the second left one-way air blowing pipe and the first right one-way air blowing pipe, as well as a spacing between center lines of adjacent horizontal sections of the first left one-way air blowing pipe, the second left one-way air blowing pipe, the center two-way air blowing pipe, the second left one-way air blowing pipe and the first right one-way air blowing pipe are same as each of five row spacings corresponding to the male parent of a six-row hybrid rice in a seed production field; and fixing each of the air blowing pipes to the lifting frame by locking bolts on the right-angle sliding sleeves;

moving the hand-held pneumatic pollinator for hybrid rice seed production to a hybrid rice seed production field, wherein the moving the hand-held pneumatic pollinator for hybrid rice seed production to a hybrid rice seed production field includes: before 10:00 when the male parent of the hybrid rice is in full bloom, driving the hand-held pneumatic pollinator for hybrid rice seed production to the seed production field, and driving the driving wheels to travel between two middle rows of the male parent, wherein the horizontal section of the center two-way air blowing pipe is parallel to two central rows of the male parent; and operating the main controller by the touch screen to control the drive controllers so as to control a rotation of the stepping motor, in such a manner that the air blowing port of each of the air blowing pipes is located at a lower middle portion of a pollen spike;

adjusting airflow parameters of the air blowing pipes, wherein the adjusting airflow parameters of the air blowing pipes includes: setting, based on airflow velocity requirements for pollination of different male parent rows of different kinds of hybrid rice, the flow velocity at the air blowing port of each of the first left one-way air blowing pipe, the second left one-way air blowing pipe, the center two-way air blowing pipe, the second left one-way air blowing pipe, and the first right one-way air blowing pipe through the touch screen of the controller; and controlling the driving controllers by the controller to drive the direct current fans to operate, wherein the airflow is output at a preset wind speed at the air blowing port of each of the air blowing pipes;

pollinating field, wherein the pollinating field includes: during a period from 10:30 to 14:30 when the male parent of the hybrid rice is in a full bloom period, after adjusting the airflow parameters of the air blowing pipes, driving the power chassis of the hand-held pneumatic pollinator for hybrid rice seed production to travel between two middle rows of the male parent, in such a manner that the first left one-way air blowing pipe, the second left one-way air blowing pipe, the center two-way air blowing pipe, the second left one-way air blowing pipe and the first right one-way air blowing pipe are located between two adjacent rows of the six-row male parent of the hybrid rice, respectively, wherein the airflows from the air blowing ports of the first left one-way air blowing pipe and the second left one-way air blowing pipe are blown leftwards to ears of two left rows of the male parent, the airflows from the air blowing ports of the second left one-way air blowing pipe and the first right one-way air blowing pipe are blown rightwards to ears of two right rows of the male parent, and the airflows from the air blowing ports located at both sides of the center two-way air blowing pipe are blown leftwards and rightwards to ears of the two middle rows of the male parent, in such a manner that the pollen of the male parent leaves a flower core and drifts with the airflow and swing of the ears; wherein the pollen of three left rows of the male parent drifts to adjacent left rows of the female parent through the left airflows, and the pollen of three right rows of the male parent drifts to adjacent right rows of the female parent through the right airflows, and as the airflow velocity above the rows of a female parent compartment gradually decreases, the pollen moves downwardly due to gravity, and a part of the pollen settles on ears of the female parent to complete the pollination; and wherein when travelling to the end of the six-row male parent in the female parent compartment, the hand-held pneumatic pollinator for hybrid rice seed production turns around in the field and travels to a six-row male parent in another adjacent male parent compartment to perform the pollination operation again, and then sequentially travels to the male parent compartment to perform the pollination operation, and wherein the pollination is performed two or three times a day from 10:30 to 14:30 during the full bloom period; and stopping for maintenance, wherein the stopping for maintenance includes: after the pollination is finished every day, controlling the drive controllers by the controller to stop the direct current fans; and driving the hand-held pneumatic pollinator for hybrid rice seed production to travel to an agricultural machinery warehouse for maintenance to prepare for the pollination of the next day.

In some embodiments of the present disclosure, the airflow velocities of the air blowing pipes are different from each other, and the airflow velocity at the air blowing port of each of the air blowing pipes is determined by measuring a flow velocity inside the air blowing pipe through one of the flow velocity sensors, and is adjusted by one of the direct current fans that is controlled by one of the driving controllers through the controller.

The present disclosure has the following beneficial effects. Each air blowing pipe acts individually on the corresponding male parent row at a set airflow velocity to blow off the pollen so as to drift toward the corresponding female parent compartment, so as to realize the directional drift of pollen in large-scale seed production, and uniform pollination, thereby solving the problem of accurate pollen spreading in large-scale seed production to provide a model for mechanized efficient pollination of the rice seed production.

REFERENCE LIST

Figure 1:
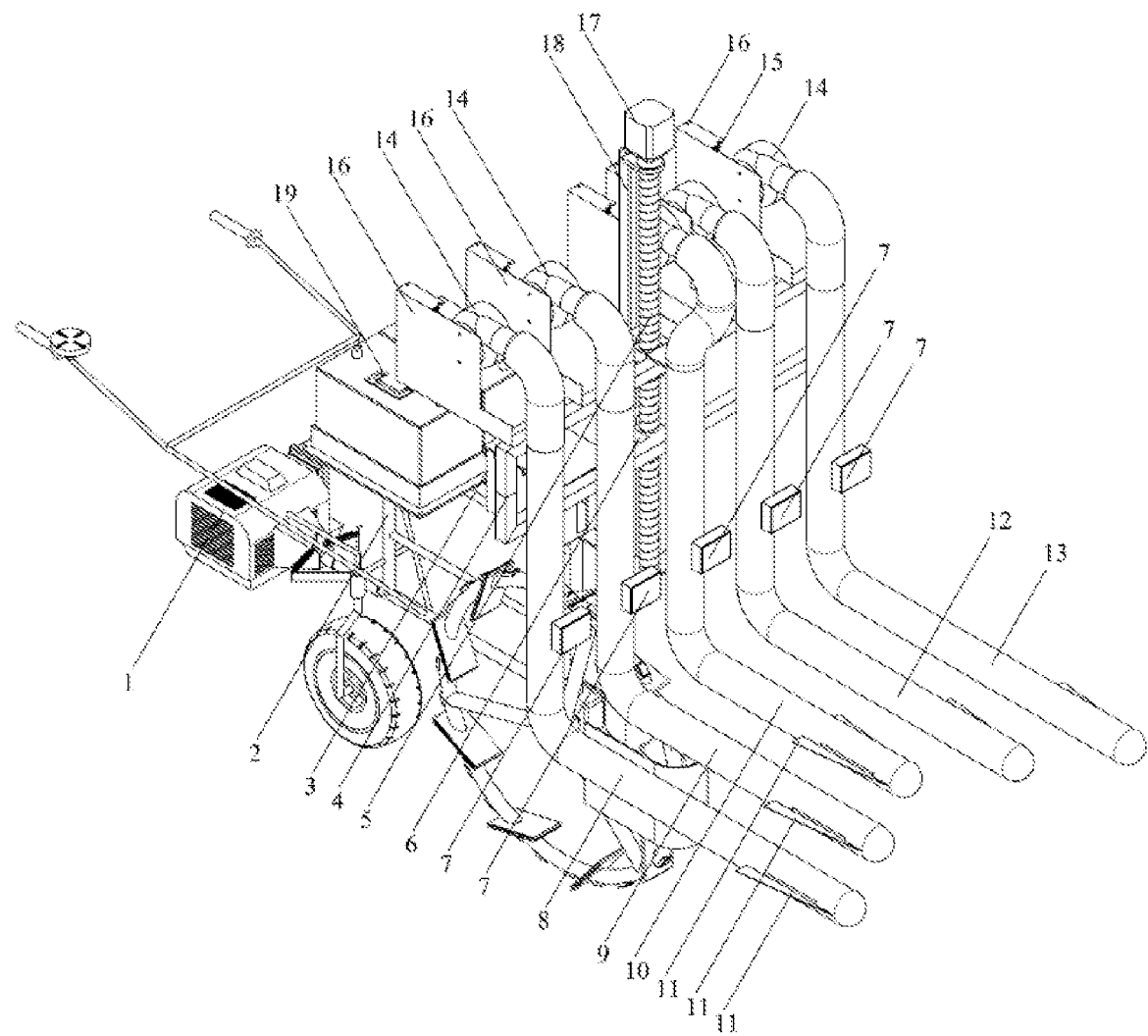
FIG. 1 is a front right isometric view of a hand-held pneumatic pollinator for hybrid rice seed production according to an embodiment of the present disclosure.

1: hand-held power chassis
   1-1: engine
   1-2: centrifugal clutch
   1-3: support wheels
   1-4: driving wheels
   1-5: decelerator
   1-6: crop divider
   1-7: armrest
2: bracket
3: controller
4: lifting frame
5: lead screw
6: ball nut
7: flow velocity sensor
8: first right one-way air blowing pipe
9: second right one-way air blowing pipe
10: center two-way air blowing pipe
11: baffle plate
12: second left one-way air blowing pipe
13: first left one-way air blowing pipe
14: DC fan
15: drive controller
16: support plate
17: stepping motor
18: guide rail
19: storage battery
20: slider
21: right-angle sliding sleeve
22: air blowing port

DESCRIPTION OF EMBODIMENTS

The present disclosure will be further described below with reference to the accompanying drawings and embodiments.

As shown in FIGS. 1 to 6, a hand-held pneumatic pollinator for hybrid rice seed production mainly includes a hand-held power chassis 1, a lifting assembly, a pneumatic pollination assembly, and a control assembly. Further, the lifting assembly and the control assembly are fixed on an upper portion of the hand-held power chassis 1, and the pneumatic pollination assembly is fixed at the front of the lifting assembly and is controlled by the lifting assembly to move upwardly and downwardly. The control assembly is configured to control the operation of the pollinator.

Figure 2:
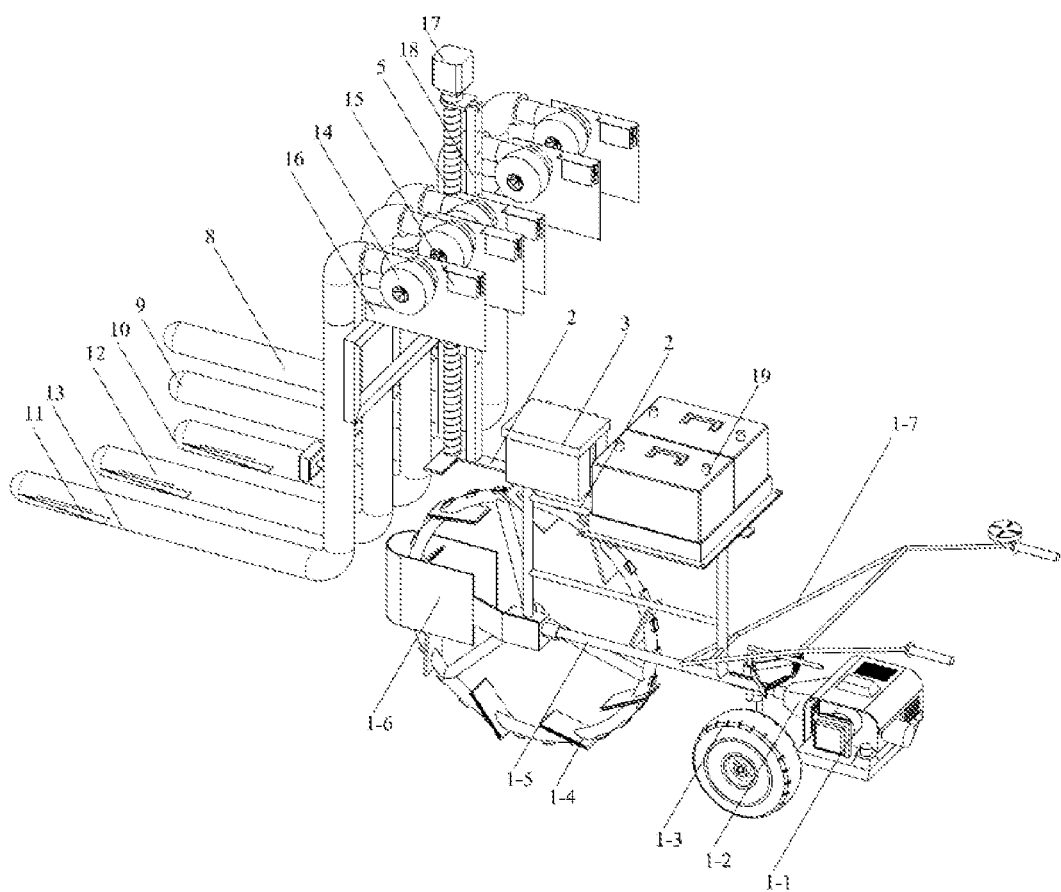
FIG. 2 is a rear left isometric view of the hand-held pneumatic pollinator for hybrid rice seed production shown in FIG. 1.

As shown in FIG. 2, the hand-held power chassis 1 includes an engine 1-1, a centrifugal clutch 1-2, support wheels 1-3, driving wheels 1-4, a decelerator 1-5, a crop divider 1-6 and armrests 1-7. A power output shaft of the engine 1-1 is connected with a power input shaft of the decelerator 1-5 by the centrifugal clutch 1-2. The driving wheels 1-4 are installed on a power output shaft of the decelerator 1-5. The support wheels 1-3 are fixed below the decelerator 1-5, and the support wheels 1-3 and the driving wheels 1-4 support a weight of the entire pollinator and drive the pollinator to travel. The armrests 1-7 are fixed on the decelerator 1-5 at a front portion thereof to allow an operator to adjust a travel direction. The crop divider 1-6 is fixed at the front of the decelerator 1-5 to prevent crops from entering the driving wheels 1-4. The lifting assembly is fixed on the decelerator 1-5 by a bracket 2.

The pneumatic pollination assembly includes a lifting frame 4, flow velocity sensors 7, a first right one-way air blowing pipe 8, a second right one-way air blowing pipe 9, a center two-way air blowing pipe 10, baffle plates 11, a second left one-way air blowing pipe 12, a first left one-way air blowing pipe 13, direct current (DC) fans 14, drive controllers 15, support plates 16, a storage battery 19 and right-angle sliding sleeves 21. Further, each of the first right one-way air blowing pipe 8, the second right one-way air blowing pipe 9, the center two-way blowing pipe 10, the second left one-way air blowing pipe 12 and the first left one-way air blowing pipe 13 is L-shaped and is formed by connecting a vertical section and a horizontal section. Further, the vertical section of each air blowing pipe has the same length. Two right-angle sliding sleeves 21 are symmetrically vertically fixed at each of the vertical sections of the first right one-way air blowing pipe 8, the second right one-way air blowing pipe 9, the center two-way air blowing pipe 10, the second left one-way air blowing pipe 12, and the first left one-way air blowing pipe 13 at the same height. Further, a distance between the two right-angle sliding sleeves 21 is the same as a width of the lifting frame 4, such that the two right-angle sliding sleeves 21 may be engaged with upper and lower ends of the lifting frame 4. The lifting frame 4 may be used as a mounting bracket for the five air blowing pipes. The first right one-way air blowing pipe 8, the second right one-way air blowing pipe 9, the center two-way air blowing pipe 10, the second left one-way air blowing pipe 12 and the first left one-way air blowing pipe 13 are sequentially and uniformly sleeved on the lifting frame 4 by the right-angle sliding sleeves 21 in a right to left direction. Relative positions of the air blowing pipes on the lifting frame 4 are adjustable laterally. When moving to target positions on the lifting frame 4, the air blowing pipes are fixed by tightening locking bolts on each of the right-angle sliding sleeves 21.

Five support plates 16 are equidistantly fixed at an upper portion of the lifting assembly. Further, five DC fans 14 are disposed in one-to-one correspondence with the five support plates 16, and are fixed at front side portions of the five support plates 16. Five drive controllers 15 are disposed in one-to-one correspondence with the five support plates 16, and are fixed at rear side portions of the five support plates 16. Air outlets of the five DC fans 14 are disposed in one-to-one correspondence with and in communication with upper portions of the first right one-way air blowing pipe 8, the second right one-way air blowing pipe 9, the center two-way air blowing pipe 10, the second left one-way air blowing pipe 12 and the first left one-way air blowing pipe 13 through hoses. These hoses can ensure that each air blowing pipe has a predetermined amount of lateral movement space. An airflow amount of each air blowing pipe can be controlled by the DC fans 14.

A front end of the horizontal section of each of the first right one-way air blowing pipe 8, the second right one-way air blowing pipe 9, the center two-way air blowing pipe 10, the second left one-way air blowing pipe 12 and the first left one-way air blowing pipe 13 is formed with at least one air blowing port 22, and an lower portion of the air blowing port is provided with a baffle plate 11 for guiding the airflow, thereby forming an airflow that causes pollen of a male parent to drift toward a female parent. A flow velocity sensor 7 is fixed at the vertical section of each of the first right one-way air blowing pipe 8, the second right one-way air blowing pipe 9, the center two-way air blowing pipe 10, the second left one-way air blowing pipe 12 and the first left one-way air blowing pipe 13 at the same height. Further, a detection end of each flow velocity sensor 7 extends into an interior center of the respective air blowing pipe to measure an airflow velocity therein. The storage battery 19 is fixed on the bracket 2 of the lifting assembly to supply the power to power consuming components.

Figure 4:
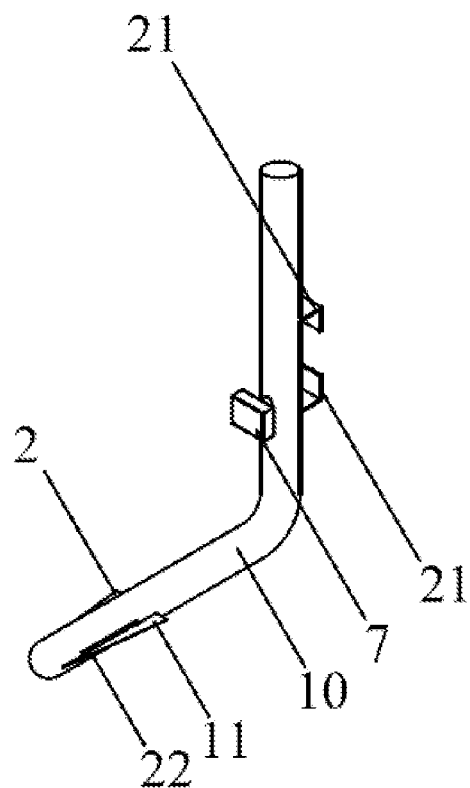
FIG. 4 is a schematic perspective view showing a structure of a central bidirectional air blowing pipe.
Figure 5:
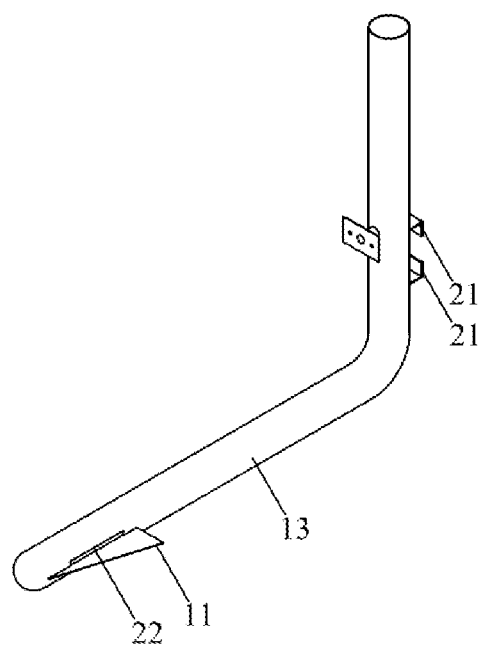
FIG. 5 is a schematic perspective view showing a structure of a first left one-way air blowing pipe.

In some embodiments of the present disclosure, in order to perform the pollination operation, the position of the air blowing port 22 in each of the first right one-way air blowing pipe 8, the second right one-way air blowing pipe 9, the center two-way air blowing pipe 10, the second left one-way air blowing pipe 12 and the first left one-way air blowing pipe 13 is required to be designed optimally. In this embodiment, the first left one-way air blowing pipe 13 and the second left one-way air blowing pipe 12 are both L-shaped and have substantially similar structures. FIG. 5 shows a schematic structural view of the first left one-way air blowing pipe 13. The air blowing port 22 is formed at a side of the front portion of the horizontal section of each of the first left one-way air blowing pipe 13 and the second left one-way air blowing pipe 12 away from the center two-way air blowing pipe 10, and an airflow blown from the air blowing port 22 directs leftwards. The air blowing port 22 is a horizontally elongated slit, which allows the airflow to generate a greater blowing force. The baffle plate 11 is fixed horizontally below the air blowing port 22, and the airflow direction can be adjusted by an angle of the baffle plate 11. In this embodiment, the baffle plate 11 is in a triangle shape, and a tip thereof faces toward a travelling direction of the pollinator, so as to reduce damage to ear of the rice during traveling. The first right one-way air blowing pipe 8 and the second right one-way air blowing pipe 9 are disposed in a mirror symmetrical structure with respect to the first left one-way air blowing pipe 13 and the second left one-way air blowing pipe 12, respectively, and a mirror symmetrical plane is a vertical center plane of the center two-way air blowing pipe 10. Therefore, the air blowing ports 22 of the first right one-way air blowing pipe 8 and the second right one-way air blowing pipe 9 are also provided at sides of front portions of the horizontal sections thereof away from the center two-way air blowing pipe 10, the baffle plate 11 is also disposed below the air blowing port 22, and an airflow blown from the air blowing port 22 directs rightwards. In addition, as shown in FIG. 4, the center two-way air blowing pipe 10 is L-shaped. Unlike that the air blowing port 22 is formed at one side of the horizontal section of each of other four air blowing pipes, air blowing ports 22 are formed at both sides of a front portion of the horizontal section of the center two-way air blowing pipe 10, and the baffle plates 11 are horizontally fixed below the air blowing ports 22, so that the air is blown toward two sides by the center two-way air blowing pipe 10.

The first left one-way air blowing pipe 13, the second left one-way air blowing pipe 12, the center two-way air blowing pipe 10, the second right one-way air blowing pipe 9 and the first right one-way air blowing pipe 8 are installed on the lifting frame 4, and the horizontal sections of these five air blowing pipes are located on the same horizontal plane with different lengths. In order to improve the effect of the pneumatic pollination, a line of connecting centers of front ends of the horizontal sections of these five air blowing pipes are in a "V" shape protruding toward the hand-held power chassis 1. The air blowing pipes on both sides have relatively long lengths, and the central air blowing pipe has a shortest length. In the five air blowing pipes, the length difference between the horizontal sections of two adjacent air blowing pipes is 1-1.5 times of the length of the air blowing port 22.

Figure 3:
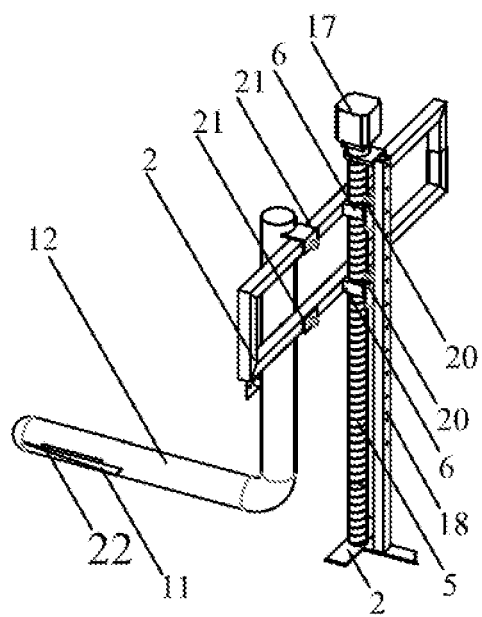
FIG. 3 is a schematic structural view of a lifting assembly of the hand-held pneumatic pollinator for hybrid rice seed production shown in FIG. 1.

As shown in FIG. 3, the lifting assembly includes the bracket 2, a guide rail 18, a lead screw 5, a stepping motor 17, and sliders 20. The guide rail 18 is vertically fixed at a front upper portion of the bracket 2, and is provided with a bearing support at an upper portion thereof. The lead screw 5 is installed on the guide rail 18 by the bearing support on the upper portion of the guide rail 18 at an upper end thereof, and is installed at a front upper portion of the bracket 2 by the bearing support at a lower end thereof. Further, the guide rail 18 is parallel to a central axis of the lead screw 5. The stepping motor 17 is fixed at an upper end of the guide rail 18, and the upper end of the lead screw 5 is coaxially fixed to and connected with an output shaft of the stepping motor 17, so that the lead screw 5 is driven to be rotated by the stepping motor 17. Ball nuts 6 are sleeved on the lead screw 5 and forms a spiral fit with the lead screw 5. The guide rail 18 is provided with the sliders 20, and the sliders 20 and the guide rail 18 constitute a moving pair. Two ball nuts 6 are fixedly connected with a middle portion of the lifting frame 4 at front portions thereof, and are fixedly connected with two sliders 20 at rear portions thereof. Thus, the two ball nuts 6 can be controlled to move upwardly and downwardly by controlling forward and reverse rotations of the stepping motor 17 to drive the pneumatic pollination assembly by the sliders 20 and the lifting frame 4 to lift upwardly and downwardly, so that the airflow from the pneumatic pollination assembly can be blown toward the ears of the male parent of different heights.

The control assembly includes a controller 3, the flow velocity sensors 7, the drive controllers 15, the storage battery 19, a 485-conversion-TTL module and a touch screen. The storage battery 19 is configured to supply the power to the controller 3 and the touch screen by a voltage regulator module. The five flow velocity sensors 7 are connected to the controller 3 by the 485-conversion-TTL module. The five drive controllers 15 are connected to the controller 3 by control lines. The storage battery 19 is connected to the five drive controllers 15 by cables. In addition, the five drive controllers 15 are connected to the five DC fans 14, respectively.

Figure 6:
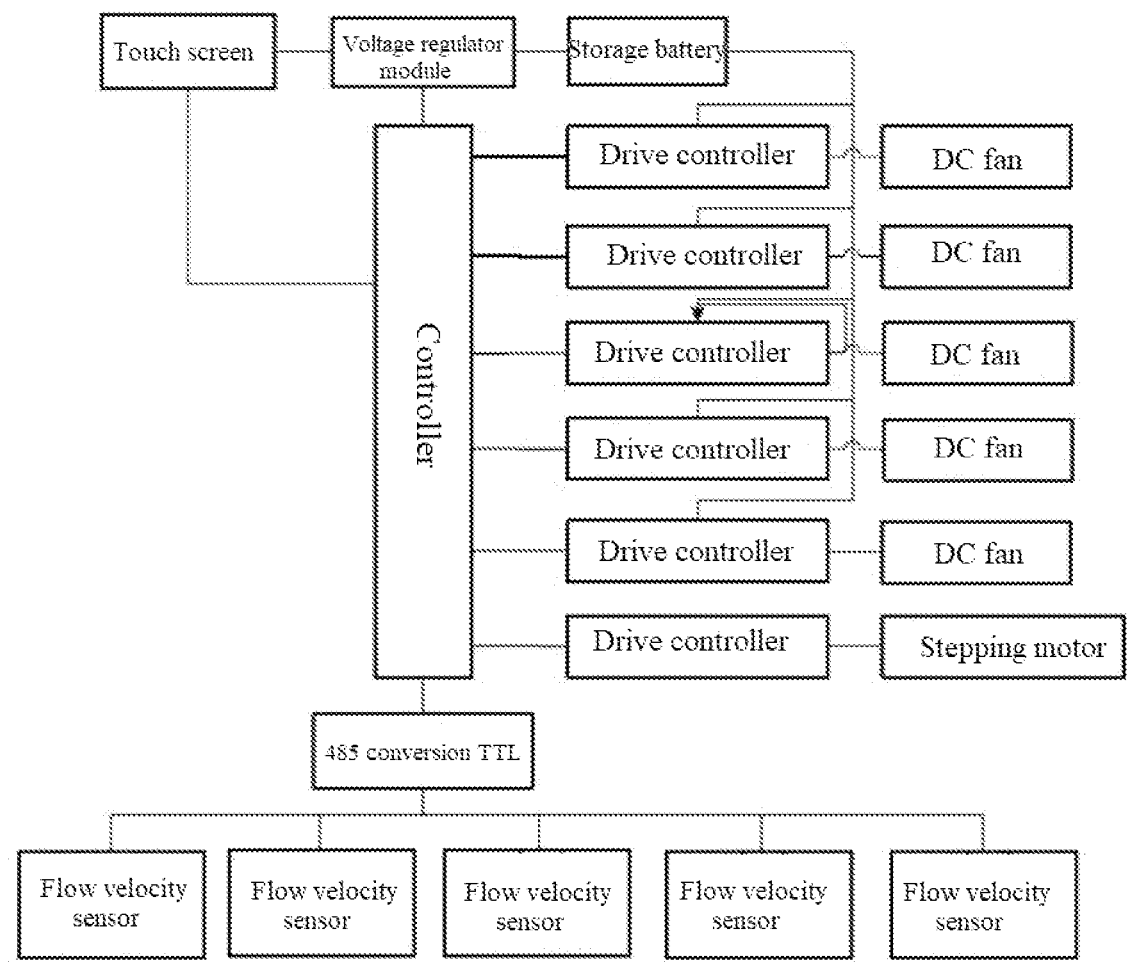
FIG. 6 is a block diagram of a composition principle of a controller.

In this embodiment, the controller 3 is implemented with a PLC control module, and its compositional principle block diagram is shown in FIG. 6. The flow velocity sensor 7 on each air blowing pipe is connected to the PLC control module by the 485-conversion-TTL module, and a Bluetooth module and the touch screen are connected with the PLC control module. The storage battery 19 supplies the power to the PLC control module and the touch screen by the voltage regulator module. The five drive controllers 15 are connected to the PLC control module by control lines. The storage battery 19 is connected to the five drive controllers 15 by cables, and the five drive controllers 15 are connected to the five DC fans 14, respectively. In addition, the Bluetooth module is configured for signal transmission with the external environment. The specific parameter setting may be carried out by the touch screen for easy operation.

Although five air blowing pipes are installed in this pollinator, the number of air blowing pipes may be actually adjusted based on a row ratio of the male parent to the female parent of the hybrid rice seed production. If the male parent is planted in four rows, the first left one-way air blowing pipe 13 and the first right one-way air blowing pipe 8 can be directly removed. If the male parent is planted in eight rows, additional air blowing pipes may be provided to accommodate eight rows of male parent rice seed production.

A pollination method using the hand-held pneumatic pollinator for hybrid rice seed production as described above will be described below. The pollination method incudes:

adjusting an arrangement of air blowing pipes including: adjusting a lateral horizontal position of the center two-way air blowing pipe 10 on the lifting frame 4, such that a longitudinal center of the center two-way air blowing pipe 10 is located on the same vertical plane as that of the hand-held pneumatic pollinator for hybrid rice seed production, that is, the longitudinal center of the center two-way air blowing pipe 10 is coincident with a longitudinal center of the driving wheels 1-4 of the hand-held power chassis 1; adjusting each of the air blowing pipes based on a row spacing of the male parent of the hybrid rice seed production, such that a spacing between center lines of adjacent horizontal sections of the first left one-way air blowing pipe 13, the second left one-way air blowing pipe 12, the second left one-way air blowing pipe 12, and the first right one-way air blowing pipe 8, as well as a spacing between center lines of adjacent horizontal sections of the first left one-way air blowing pipe 13, the second left one-way air blowing pipe 12, the center two-way air blowing pipe 10, the second left one-way air blowing pipe 12 and the first right one-way air blowing pipe 8 are same as each of five row spacings corresponding to a male parent of a six-row hybrid rice in a seed production field; and thereafter, fixing each air blowing pipe to the lifting frame 4 by locking bolts on the right-angle sliding sleeves 21;

moving the hand-held pneumatic pollinator for hybrid rice seed production to a hybrid rice seed production field including: before 10:00 when the male parent of the hybrid rice is in full bloom, driving the hand-held pneumatic pollinator for hybrid rice seed production to the seed production field, and driving the driving wheels to travel between two middle rows of the male parent, wherein the horizontal section of the center two-way air blowing pipe 10 is parallel to two central rows of the male parent; and operating the controller 3 by the touch screen to control the drive controllers so as to control a rotation of the stepping motor 17 so that the air blowing port of each air blowing pipe is located at a lower middle portion of a pollen spike;

adjusting airflow parameters of the air blowing pipes including: setting, based on airflow velocity requirements for pollination of different male parent rows of different kinds of hybrid rice, the flow velocity at the air blowing port 22 of each of the first left one-way air blowing pipe 13, the second left one-way air blowing pipe 12, the center two-way air blowing pipe 10, the second left one-way air blowing pipe 12, and the first right one-way air blowing pipe 8 by the touch screen of the controller 3, respectively; and controlling the driving controllers 15 by the controller 3 to drive the five DC fans 14 to operate, wherein the airflow is output at a preset wind speed at the air blowing port 22 of each air blowing pipe;

pollinating field including: during a period from 10:30 to 14:30 when the male parent of the hybrid rice is in full bloom, after adjusting the airflow parameters of the air blowing pipes, driving the power chassis of the hand-held pneumatic pollinator for hybrid rice seed production to travel between the two middle rows of the male parent, such that the first left one-way air blowing pipe 13, the second left one-way air blowing pipe 12, the center two-way air blowing pipe 10, the second left one-way air blowing pipe 12 and the first right one-way air blowing pipe 8 are located between two adjacent rows of the six-row male parent of the hybrid rice, respectively, wherein the airflows from the air blowing ports 22 of the first left one-way air blowing pipe 13 and the second left one-way air blowing pipe 12 are blown leftwards to ears of two left rows of the male parent, the airflows from the air blowing ports 22 of the second left one-way air blowing pipe 12 and the first right one-way air blowing pipe 8 are blown rightwards to ears of two right rows of the male parent, and the airflows from the air blowing ports 22 at both sides of the center two-way air blowing pipe 10 are blown leftwards and rightwards to ears of the two middle rows of the male parent, in this way, the pollen of the male parent leaves a flower core and drifts with the airflow and swing of the ears; wherein the pollen of three left rows of the male parent drifts to adjacent left rows of the female parent by the left airflows, and the pollen of three right rows of the male parent drifts to adjacent right rows of the female parent by the right airflows, and as the airflow velocity above the rows of the female parent compartment gradually decreases, the pollen moves downwardly due to gravity, and a part of the pollen settles on ears of the female parent to complete the pollination; and wherein when travelling to the end of the six-row male parent in this compartment, the hand-held pneumatic pollinator for hybrid rice seed production turns around in the field and travels to six-row male parent in another adjacent compartment to perform the pollination operation again, and then sequentially travels to each male parent compartment to perform the pollination operation, in addition, the pollination is performed two or three times a day from 10:30 to 14:30 during the full bloom period; and stopping for maintenance including: after the pollination is finished every day, controlling the drive controllers 15 by the controller 3 to stop the five DC fans 14; and driving the hand-held pneumatic pollinator for hybrid rice seed production to travel to an agricultural machinery warehouse for maintenance as required to prepare for the pollination of the next day.

Since the air blowing pipes have different airflow velocities, the airflow velocity at each of the air blowing port 22 of the air blowing pipes is determined by measuring a flow velocity inside the air blowing pipe through the flow velocity sensor 7, and is adjusted by one of the DC fans 14 that is controlled by one of the driving controller 15 through the controller 3.

In addition, in the present disclosure, the five pollination pipes are provided to disperse and transport the pollen from the six-row male parent. In some embodiments of the present disclosure, three pollination pipes may be provided for a four-row male parent, or seven pollination pipes may be provided for a eight-row female parent, or the like.

The above embodiments are only some embodiments of the present disclosure and are not intended to limit the present disclosure thereto. Any minor modifications, equivalent substitutions and improvements made within the spirit and principle of the present disclosure shall fall within the scope thereof

What is claimed is:

1. A hand-held pneumatic pollinator for hybrid rice seed production, comprising:
   a hand-held power chassis;
   a lifting assembly;
   a pneumatic pollination assembly; and
   a control assembly,
   wherein the lifting assembly and the control assembly are fixed at an upper portion of the hand-held power chassis, and the pneumatic pollination assembly is fixed at the front of the lifting assembly and is controlled by the lifting assembly to move upwardly and downwardly;
   wherein the hand-held power chassis comprises an engine, a centrifugal clutch, support wheels, driving wheels, a decelerator, a crop divider and armrests, a power output shaft of the engine is connected to a power input shaft of the decelerator by the centrifugal clutch, the driving wheels are installed on a power output shaft of the decelerator, the support wheels are fixed below the decelerator, front portions of the armrests are fixed on the decelerator, the crop divider is fixed at the front of the decelerator, and the lifting assembly is fixed on the decelerator by a bracket;
   wherein the pneumatic pollination assembly comprises a lifting frame, flow velocity sensors, a first right one-way air blowing pipe, a second right one-way air blowing pipe, a center two-way air blowing pipe, baffle plates, a second left one-way air blowing pipe, a first left one-way air blowing pipe, direct current fans, drive controllers, support plates, a storage battery, and right-angle sliding sleeves, wherein each of the first right one-way air blowing pipe, the second right one-way air blowing pipe, the center two-way blowing pipe, the second left one-way blowing pipe and the first left one-way blowing pipe is L-shaped and has a vertical section with a same length, two right-angle sliding sleeves are symmetrically and vertically fixed at each of the vertical sections of the first right one-way air blowing pipe, the second right one-way air blowing pipe, the center two-way air blowing pipe, the second left one-way air blowing pipe, and the first left one-way air blowing pipe at a same height, and a distance between the two right-angle sliding sleeves is same as a width of the lifting frame, and wherein the first right one-way air blowing pipe, the second right one-way air blowing pipe, the center two-way air blowing pipe, the second left one-way air blowing pipe and the first left one-way air blowing pipe are sequentially sleeved on the lifting frame through the right-angle sliding sleeves in a right to left direction and are equidistant from each other;
   wherein the support plates are equidistantly fixed at an upper portion of the lifting assembly, the direct current fans are fixed at front side portions of the support plates, respectively, the drive controllers are fixed at rear side portions of the support plates, respectively, an air outlet of one of the direct current fans communicate with an upper portion of one of the first right one-way air blowing pipe, the second right one-way air blowing pipe, the center two-way air blowing pipe, the second left one-way air blowing pipe, and the first left one-way air blowing pipe through a hose;
   wherein a front end of a horizontal section of each of the first right one-way air blowing pipe, the second right one-way air blowing pipe, the center two-way air blowing pipe, the second left one-way air blowing pipe, and the first left one-way air blowing pipe is provided with an air blowing port, and an lower portion of the air blowing port is provided with a baffle plate configured to form an airflow, which causes pollen of a male parent to drift to a female parent, wherein a flow velocity sensor is fixed at the vertical section of each of the first right one-way air blowing pipe, the second right one-way air blowing pipe, the center two-way air blowing pipe, the second left one-way air blowing pipe, and the first left one-way air blowing pipe at a same height, a detection end of the flow velocity sensor extends into an interior of the air blowing pipe where the flow velocity sensor is located, to measure an airflow velocity therein, and the storage battery is fixed on the bracket of the lifting assembly;
   wherein the lifting assembly comprises the bracket, a guide rail, a lead screw, a stepping motor, and sliders, wherein the guide rail is vertically fixed at a front upper portion of the bracket and an upper portion of the guide rail is provided with a bearing support, an upper end of the lead screw is installed on the guide rail through the bearing support located at the upper portion of the guide rail, a lower end of the lead screw is installed on a front upper portion of the bracket through the bearing support, the guide rail is parallel to a central axis of the lead screw, the stepping motor is fixed at an upper end of the guide rail, the upper end of the lead screw is coaxially fixed to and connected with an output shaft of the stepping motor, and ball nuts are sleeved on the lead screw and forms a spiral fit with the lead screw; and the guide rail is provided with the sliders, the sliders and the guide rail constitute a moving pair, front portions of the ball nuts are fixedly connected to a middle portion of the lifting frame, and rear portions of the ball nuts are fixedly connected to the sliders; and
   wherein the control assembly comprises a controller, flow velocity sensors, drive controllers, a storage battery, a 485-conversion-TTL module, and a touch screen, wherein the storage battery is configured to supply a power to the controller and the touch screen through a voltage regulator module, the flow velocity sensors are connected to the controller through the 485-conversion-TTL module, the drive controllers are connected to the controller through control lines, the storage battery is connected to the drive controllers through cables, and one of the drive controllers are connected to one of the five direct current fans.

2. The hand-held pneumatic pollinator for hybrid rice seed production according to claim 1, wherein each of the first left one-way air blowing pipe and the second left one-way air blowing pipe is L-shaped, an air blowing port is provided at a side of a front portion of the horizontal section of each of the first left one-way air blowing pipe and the second left one-way air blowing pipe facing away from the center two-way air blowing pipe, the air blowing port is a horizontally elongated slit, and the baffle plate is fixed horizontally below the air blowing port and has a triangle shape; and
   the first right one-way air blowing pipe and the second right one-way air blowing pipe are disposed in a mirror symmetrical structure with respect to the first left one-way air blowing pipe and the second left one-way air blowing pipe, respectively.

3. The hand-held pneumatic pollinator for hybrid rice seed production according to claim 1, wherein the center two-way air blowing pipe is L-shaped, an air blowing port is provided at each of both sides of a front portion of the horizontal section of the center two-way air blowing pipe, and the baffle plates are horizontally fixed below the air blowing ports.

4. The hand-held pneumatic pollinator for hybrid rice seed production according to claim 1, wherein the first left one-way air blowing pipe, the second left one-way air blowing pipe, the center two-way air blowing pipe, the second right one-way air blowing pipe, and the first right one-way air blowing pipe are installed on the lifting frame and are located on a same plane, and a line of connecting center lines of front end of the horizontal sections of the first left one-way air blowing pipe, the second left one-way air blowing pipe, the center two-way air blowing pipe, the second right one-way air blowing pipe and the first right one-way air blowing pipe is in a "V" shape protruding toward the hand-held power chassis.

5. The hand-held pneumatic pollinator for hybrid rice seed production according to claim 4, wherein a length difference between the horizontal sections of two adjacent ones of the first left one-way air blowing pipe, the second left one-way air blowing pipe, the center two-way air blowing pipe, the second right one-way air blowing pipe and the first right one-way air blowing pipe is 1-1.5 times of a length of the air blowing port.

6. A pollination method using a hand-held pneumatic pollinator for hybrid rice seed production
wherein the hand-held pneumatic pollinator for hybrid rice seed production, comprises:
a hand-held power chassis;
a lifting assembly;
a pneumatic pollination assembly; and
a control assembly,
wherein the lifting assembly and the control assembly are fixed at an upper portion of the hand-held power chassis, and the pneumatic pollination assembly is fixed at the front of the lifting assembly and is controlled by the lifting assembly to move upwardly and downwardly;
wherein the hand-held power chassis comprises an engine, a centrifugal clutch, support wheels, driving wheels, a decelerator, a crop divider and armrests, a power output shaft of the engine is connected to a power input shaft of the decelerator by the centrifugal clutch, the driving wheels are installed on a power output shaft of the decelerator, the support wheels are fixed below the decelerator, front portions of the armrests are fixed on the decelerator, the crop divider is fixed at the front of the decelerator, and the lifting assembly is fixed on the decelerator by a bracket;
wherein the pneumatic pollination assembly comprises a lifting frame, flow velocity sensors, a first right one-way air blowing pipe, a second right one-way air blowing pipe, a center two-way air blowing pipe, baffle plates, a second left one-way air blowing pipe, a first left one-way air blowing pipe, direct current fans, drive controllers, support plates, a storage battery, and right-angle sliding sleeves, wherein each of the first right one-way air blowing pipe, the second right one-way air blowing pipe, the center two-way blowing pipe, the second left one-way blowing pipe and the first left one-way blowing pipe is L-shaped and has a vertical section with a same length, two right-angle sliding sleeves are symmetrically and vertically fixed at each of the vertical sections of the first right one-way air blowing pipe, the second right one-way air blowing pipe, the center two-way air blowing pipe, the second left one-way air blowing pipe, and the first left one-way air blowing pipe at a same height, and a distance between the two right-angle sliding sleeves is same as a width of the lifting frame, and wherein the first right one-way air blowing pipe, the second right one-way air blowing pipe, the center two-way air blowing pipe, the second left one-way air blowing pipe and the first left one-way air blowing pipe are sequentially sleeved on the lifting frame through the right-angle sliding sleeves in a right to left direction and are equidistant from each other;
wherein the support plates are equidistantly fixed at an upper portion of the lifting assembly, the direct current fans are fixed at front side portions of the support plates, respectively, the drive controllers are fixed at rear side portions of the support plates, respectively, an air outlet of one of the direct current fans communicate with an upper portion of one of the first right one-way air blowing pipe, the second right one-way air blowing pipe, the center two-way air blowing pipe, the second left one-way air blowing pipe, and the first left one-way air blowing pipe through a hose;
wherein a front end of a horizontal section of each of the first right one-way air blowing pipe, the second right one-way air blowing pipe, the center two-way air blowing pipe, the second left one-way air blowing pipe, and the first left one-way air blowing pipe is provided with an air blowing port, and an lower portion of the air blowing port is provided with a baffle plate configured to form an airflow, which causes pollen of a male parent to drift to a female parent, wherein a flow velocity sensor is fixed at the vertical section of each of the first right one-way air blowing pipe, the second right one-way air blowing pipe, the center two-way air blowing pipe, the second left one-way air blowing pipe, and the first left one-way air blowing pipe at a same height, a detection end of the flow velocity sensor extends into an interior of the air blowing pipe where the flow velocity sensor is located, to measure an airflow velocity therein, and the storage battery is fixed on the bracket of the lifting assembly;
wherein the lifting assembly comprises the bracket, a guide rail, a lead screw, a stepping motor, and sliders, wherein the guide rail is vertically fixed at a front upper portion of the bracket and an upper portion of the guide rail is provided with a bearing support, an upper end of the lead screw is installed on the guide rail through the bearing support located at the upper portion of the guide rail, a lower end of the lead screw is installed on a front upper portion of the bracket through the bearing support, the guide rail is parallel to a central axis of the lead screw, the stepping motor is fixed at an upper end of the guide rail, the upper end of the lead screw is coaxially fixed to and connected with an output shaft of the stepping motor, and ball nuts are sleeved on the lead screw and forms a spiral fit with the lead screw; and the guide rail is provided with the sliders, the sliders and the guide rail constitute a moving pair, front portions of the ball nuts are fixedly connected to a middle portion of the lifting frame, and rear portions of the ball nuts are fixedly connected to the sliders; and
wherein the control assembly comprises a controller, flow velocity sensors, drive controllers, a storage battery, a 485-conversion-TTL module, and a touch screen, wherein the storage battery is configured to supply a power to the controller and the touch screen through a voltage regulator module, the flow velocity sensors are connected to the controller through the 485-conversion-TTL module, the drive controllers are connected to the controller through control lines, the storage battery is connected to the drive controllers through cables, and one of the drive controllers are connected to one of the five direct current fans;

wherein each of the first left one-way air blowing pipe and the second left one-way air blowing pipe is L-shaped, an air blowing port is provided at a side of a front portion of the horizontal section of each of the first left one-way air blowing pipe and the second left one-way air blowing pipe facing away from the center two-way air blowing pipe, the air blowing port is a horizontally elongated slit, and the baffle plate is fixed horizontally below the air blowing port and has a triangle shape; and the first right one-way air blowing pipe and the second right one-way air blowing pipe are disposed in a mirror symmetrical structure with respect to the first left one-way air blowing pipe and the second left one-way air blowing pipe, respectively;

wherein the method comprises:

adjusting an arrangement of air blowing pipes, wherein the adjusting the arrangement of air blowing pipes comprises: adjusting a lateral horizontal position of the center two-way air blowing pipe on the lifting frame in such a manner that a longitudinal center of the center two-way air blowing pipe is located on a same vertical plane as a longitudinal central plane of the hand-held pneumatic pollinator for hybrid rice seed production, the longitudinal center of the center two-way air blowing pipe is coincident with a longitudinal central plane of the driving wheels of the hand-held power chassis; adjusting each of the air blowing pipes based on a row spacing of the male parent of the hybrid rice seed production in such a manner that a spacing between center lines of adjacent horizontal sections of the first left one-way air blowing pipe, the second left one-way air blowing pipe, the second left one-way air blowing pipe and the first right one-way air blowing pipe, as well as a spacing between center lines of adjacent horizontal sections of the first left one-way air blowing pipe, the second left one-way air blowing pipe, the center two-way air blowing pipe, the second left one-way air blowing pipe and the first right one-way air blowing pipe are same as each of five row spacings corresponding to the male parent of a six-row hybrid rice in a seed production field; and fixing each of the air blowing pipes to the lifting frame by locking bolts on the right-angle sliding sleeves;

moving the hand-held pneumatic pollinator for hybrid rice seed production to a hybrid rice seed production field, wherein the moving the hand-held pneumatic pollinator for hybrid rice seed production to a hybrid rice seed production field comprises: before 10:00 AM of a day when the male parent of the hybrid rice is in full bloom, driving the hand-held pneumatic pollinator for hybrid rice seed production to the seed production field, and driving the driving wheels to travel between two middle rows of the male parent, wherein the horizontal section of the center two-way air blowing pipe is parallel to two central rows of the male parent; and operating the controller by the touch screen to control the drive controllers so as to control a rotation of the stepping motor, in such a manner that the air blowing port of each of the air blowing pipes is located at a lower middle portion of a pollen spike;

adjusting airflow parameters of the air blowing pipes, wherein the adjusting airflow parameters of the air blowing pipes comprises: setting, based on airflow velocity requirements for pollination of different male parent rows of different kinds of hybrid rice, the flow velocity at the air blowing port of each of the first left one-way air blowing pipe, the second left one-way air blowing pipe, the center two-way air blowing pipe, the second left one-way air blowing pipe, and the first right one-way air blowing pipe through the touch screen of the controller; and controlling the driving controllers by the controller to drive the direct current fans to operate, wherein the airflow is output at a preset wind speed at the air blowing port of each of the air blowing pipes;

pollinating field, wherein the pollinating field comprises: during a period from 10:30 AM to 2:30 PM of the day when the male parent of the hybrid rice is in a full bloom period, after adjusting the airflow parameters of the air blowing pipes, driving the power chassis of the hand-held pneumatic pollinator for hybrid rice seed production to travel between two middle rows of the male parent, in such a manner that the first left one-way air blowing pipe, the second left one-way air blowing pipe, the center two-way air blowing pipe, the second left one-way air blowing pipe and the first right one-way air blowing pipe are located between two adjacent rows of the six-row male parent of the hybrid rice, respectively, wherein the airflows from the air blowing ports of the first left one-way air blowing pipe and the second left one-way air blowing pipe are blown leftwards to ears of two left rows of the male parent, the airflows from the air blowing ports of the second left one-way air blowing pipe and the first right one-way air blowing pipe are blown rightwards to ears of two right rows of the male parent, and the airflows from the air blowing ports located at both sides of the center two-way air blowing pipe are blown leftwards and rightwards to ears of the two middle rows of the male parent, in such a manner that the pollen of the male parent leaves a flower core and drifts with the airflow and swing of the ears; wherein the pollen of three left rows of the male parent drifts to adjacent left rows of the female parent through the left airflows, and the pollen of three right rows of the male parent drifts to adjacent right rows of the female parent through the right airflows, and as the airflow velocity above the rows of a female parent compartment gradually decreases, the pollen moves downwardly due to gravity, and a part of the pollen settles on ears of the female parent to complete the pollination; and wherein when travelling to the end of the six-row male parent in the female parent compartment, the hand-held pneumatic pollinator for hybrid rice seed production turns around in the field and travels to a six-row male parent in another adjacent male parent compartment to perform the pollination operation again, and then sequentially travels to the male parent compartment to perform the pollination operation, and wherein the pollination is performed two or three times a day from 10:30 AM to 2:30 PM of the day during the full bloom period; and stopping for maintenance, wherein the stopping for maintenance comprises: after the pollination is finished every day, controlling the drive controllers by the controller to stop the direct current fans; and driving the hand-held pneumatic pollinator for hybrid rice seed production to travel to an agricultural machinery warehouse for maintenance to prepare for the pollination of the next day.

7. The pollination method according to claim 6, wherein the airflow velocities of the air blowing pipes are different from each other, and the airflow velocity at the air blowing port of each of the air blowing pipes is determined by measuring a flow velocity inside the air blowing pipe through one of the flow velocity sensors, and is adjusted by one of the direct current fans that is controlled by one of the driving controllers through the controller.

\* \* \* \* \*